US009888991B2

(12) United States Patent
Zoll et al.

(10) Patent No.: US 9,888,991 B2
(45) Date of Patent: Feb. 13, 2018

(54) COMPOSITIONS, DEVICES, KITS AND METHODS FOR ATTACHING SURGICAL MESHES TO TISSUE

(71) Applicant: Boston Scientific Scimed, Inc., Maple Grove, MN (US)

(72) Inventors: Jonathan Zoll, Providence, RI (US); Peter J. Pereira, Mendon, MA (US); Boris Shapeton, Natick, MA (US); John Edward Sherry, Needham, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 45 days.

(21) Appl. No.: 14/564,370

(22) Filed: Dec. 9, 2014

(65) Prior Publication Data

US 2015/0157439 A1    Jun. 11, 2015

Related U.S. Application Data

(60) Provisional application No. 61/913,736, filed on Dec. 9, 2013.

(51) Int. Cl.
*A61F 2/00* (2006.01)
*A61L 31/10* (2006.01)
*A61L 31/14* (2006.01)

(52) U.S. Cl.
CPC ............ *A61F 2/0063* (2013.01); *A61L 31/10* (2013.01); *A61L 31/14* (2013.01); *A61F 2002/0068* (2013.01); *A61F 2002/0072* (2013.01); *A61F 2250/0001* (2013.01); *A61F 2310/00401* (2013.01); *A61F 2310/00437* (2013.01); *A61F 2310/00568* (2013.01); *A61F 2310/00982* (2013.01); *A61F 2310/00988* (2013.01); *A61L 2430/34* (2013.01)

(58) Field of Classification Search
CPC ... A61F 2/0063; A61F 2002/0068–2002/0072; A61F 2310/00389–2310/00976; A61F 2/848; A61F 2310/00982; A61F 2310/00988; A61F 2250/0001; A61L 21/00–21/14; A61L 31/10; A61L 31/14; A61L 2430/34
USPC ................... 600/29, 30, 37; 128/897–899
See application file for complete search history.

(56) References Cited

U.S. PATENT DOCUMENTS

| 5,292,362 | A | * | 3/1994 | Bass | ............... A61B 17/00491 106/173.01 |
| 5,552,452 | A | * | 9/1996 | Khadem | ............... A61L 24/106 522/2 |
| 5,922,026 | A | | 7/1999 | Chin | |
| 6,372,228 | B1 | * | 4/2002 | Gregory | ............... A61F 2/0063 424/400 |

(Continued)

OTHER PUBLICATIONS

Final Office Action for U.S. Appl. No. 14/614,669, dated Sep. 23, 2016, 15 pages.

*Primary Examiner* — Navin Natnithithadha
*Assistant Examiner* — Sunita Reddy
(74) *Attorney, Agent, or Firm* — Brake Hughes Bellermann LLP (57) ABSTRACT

The present disclosure is directed to methods, compositions, devices and kits which pertain to the attachment of surgical meshes to tissue by application of an energy source to the meshes and tissue in the presence of a bonding material.

18 Claims, 3 Drawing Sheets

(56) References Cited

U.S. PATENT DOCUMENTS

| | | | | |
|---|---|---|---|---|
| 6,391,049 B1* | 5/2002 | McNally | A61B 17/00491 | 606/214 |
| 6,875,427 B1* | 4/2005 | DeVore | A61K 38/39 | 128/898 |
| 2003/0114866 A1* | 6/2003 | Ulmsten | A61F 2/0045 | 606/151 |
| 2003/0191480 A1* | 10/2003 | Ulmsten | A61F 2/0045 | 606/151 |
| 2004/0215231 A1* | 10/2004 | Fortune | A61B 17/0057 | 606/213 |
| 2004/0236371 A1* | 11/2004 | McNally-Heintzelman | A61L 24/0094 | 606/213 |
| 2005/0010239 A1* | 1/2005 | Chefitz | A61F 2/0063 | 606/151 |
| 2006/0195010 A1* | 8/2006 | Arnal | A61B 17/06066 | 600/30 |
| 2008/0004686 A1* | 1/2008 | Hunt | A61F 2/2418 | 623/1.11 |
| 2009/0304773 A1* | 12/2009 | Milbocker | A61L 24/043 | 424/423 |
| 2010/0104608 A1* | 4/2010 | Abuzaina | A61L 15/42 | 424/400 |
| 2012/0271290 A1 | 10/2012 | Sargeant et al. | | |
| 2013/0190245 A1* | 7/2013 | Soltz | A61L 24/001 | 514/17.2 |
| 2013/0225918 A1* | 8/2013 | Harrah | A61F 2/0036 | 600/37 |
| 2014/0309626 A1 | 10/2014 | Sargeant et al. | | |
| 2015/0216646 A1* | 8/2015 | Zoll | A61F 2/0045 | 600/30 |
| 2015/0265387 A1* | 9/2015 | Alexander | A61B 17/3468 | 600/37 |
| 2015/0314035 A1 | 11/2015 | Rolfes et al. | | |
| 2015/0374516 A1* | 12/2015 | Pereira | A61F 2/848 | 623/1.12 |

\* cited by examiner

Fig. 8

COMPOSITIONS, DEVICES, KITS AND METHODS FOR ATTACHING SURGICAL MESHES TO TISSUE

STATEMENT OF RELATED APPLICATION

This application claims the benefit of U.S. Provisional Application Ser. No. 61/913,736, filed Dec. 9, 2013 and entitled "COMPOSITIONS, DEVICES, KITS AND METHODS FOR ATTACHING SURGICAL MESHES TO TISSUE," the entire disclosure of which is hereby incorporated by reference in its entirety.

FIELD OF THE INVENTION

The present invention relates to methods, compositions, devices and kits for the attachment of surgical meshes to tissue.

BACKGROUND

Pelvic floor disorders are highly prevalent among women and involve a dropping down (prolapse) of the bladder, rectum and/or uterus caused by weakness of or injury to the ligaments, connective tissue, and muscles of the pelvis. The different types of pelvic floor disorders are commonly named according to the organ affected. For example, a rectocele develops when the rectum drops down and protrudes into the back wall of the vagina. An enterocele develops when the small intestine and the lining of the abdominal cavity (peritoneum) bulge downward between the uterus and the rectum or, if the uterus has been removed, between the bladder and the rectum. A cystocele develops when the bladder drops down and protrudes into the front wall of the vagina. In prolapse of the uterus (procidentia), the uterus drops down into the vagina. Pelvic floor disorders are commonly treated by implanting a surgical mesh within the patient's pelvis to support the organ or organs that require support.

Surgical meshes are also employed in various other soft tissue applications. As one example, urinary incontinence affects millions of men and women of all ages in the United States. Stress urinary incontinence (SUI) affects primarily women and is generally caused by two conditions, intrinsic sphincter deficiency (ISD) and hypermobility. These conditions may occur independently or in combination. In ISD, the urinary sphincter valve, located within the urethra, fails to close properly (coapt), causing urine to leak out of the urethra during stressful activity. Hypermobility is a condition in which the pelvic floor is distended, weakened, or damaged, causing the bladder neck and proximal urethra to rotate and descend in response to increases in intra-abdominal pressure (e.g., due to sneezing, coughing, straining, etc.). The result is that there is an insufficient response time to promote urethral closure and, consequently, urine leakage and/or flow results. A common treatment of SUI is via the use of a surgical mesh, commonly referred to as a sling, which is permanently placed under a patient's bladder neck or mid-urethra to provide a urethral platform. Placement of the sling limits the endopelvic fascia drop, while providing compression to the urethral sphincter to improve coaptation.

The present invention pertains to methods, compositions, devices and kits that are useful in treating these and other disorders, diseases and conditions.

SUMMARY OF THE INVENTION

The present invention relates to methods, compositions, devices and kits for the attachment of surgical meshes to tissue.

In accordance with some aspects of the present disclosure, methods of attaching a urogynecological surgical mesh to patient tissue are provided which comprise placing a mesh material and a bonding material in contact with patient tissue and using energy from an energy source to apply energy to said bonding material, such that the bonding material is activated and the mesh material is attached to the tissue.

According to other aspects of the disclosure, urogynecological surgical meshes are provided which comprise a mesh material and a bonding material associated with the mesh material, wherein the surgical mesh is configured to bond to patient tissue when exposed to an energy source while the surgical mesh is in contact with said tissue.

According to still other aspects of the invention, kits are provided, which comprise any combination of two or more of the following items: (a) a surgical mesh, either without or with an associated bonding material, (b) a bonding material in solid form or in fluid form (e.g., in liquid form, gel form or paste form), (c) a surgical instrument configured to hold and place a surgical mesh, (d) an energy source, and (e) printed material with one or more of the following: (i) storage information and (ii) instructions regarding how to implant the surgical mesh in a subject.

These and other aspects, as well as various embodiments and advantages of the present invention will become immediately apparent to those of ordinary skill in the art upon review of the Detailed Description and claims to follow.

DETAILED DESCRIPTION

A more complete understanding of the present invention is available by reference to the following detailed description of numerous aspects and embodiments of the invention. The detailed description which follows is intended to illustrate but not limit the invention.

In various beneficial embodiments, tissue bonding technology is used as a technique for attaching surgical meshes to tissue. This is achieved by placing a mesh material and a bonding material in intimate association with patient tissue and then applying energy from an energy source to activate the bonding material and bond the mesh to the tissue. In this way, the present disclosure provides for the attachment of surgical mesh to patient tissue without the use of sutures, staples or other mechanical fasteners.

As discussed in more detail below, in some embodiments, the mesh material and bonding material may be applied separately to the tissue. In other embodiments, the mesh material and bonding material may be combined when applied to tissue, for example, by providing a coating of a bonding material on all or a portion of a mesh material or by incorporating a bonding material into all or a portion of a mesh material, among other strategies.

Different energy sources may be used for mesh attachment, depending on the mechanism for tissue bonding that is employed. The energy source may be, for example, a source of heat or light, such as a laser or a light-emitting diode (LED). Infrared and near-infrared laser sources include carbon dioxide ($CO_2$), thulium-holmium-chromium, holmium, thulium, and neodymium rare-earth-doped-garnets (THC:YAG, Ho:YAG, Tm:YAG, and Nd:YAG, respectively), and gallium aluminium arsenide diode (GaAlAs) lasers, among others. Visible sources include potassium-titanyl phosphate (KTP) frequency-doubled Nd:YAG, and argon lasers, among others. Other energy sources include radiofrequency sources (e.g., a microwave source), radiation sources (e.g., x-ray radiation, gamma radiation, etc.), or a locally produced plasma. Argon plasmas are currently employed in various medical applications, including argon beam coagulators, which ionize argon gas to form an argon plasma and then use the plasma to deliver thermal energy to nearby tissue. In the present disclosure, an argon beam may be used as a source of heat for tissue bonding. Other energy sources include radiation (e.g., x-ray radiation, gamma radiation, etc.).

In certain embodiments, the energy source is a handheld energy source.

In certain embodiments, the energy source is provided in a stand-alone unit. In other embodiments, the energy source is combined with another device. For example, the energy source may be combined with a mesh delivery device, thereby creating a single unit that can hold, place and seal a mesh to tissue.

In some embodiments, the energy source is connected to a control unit, which controls the energy emitting from the energy source. Preferably, the amount of energy is sufficient to activate the bonding material without significantly damaging the underlying tissue. In some embodiments, the control unit is designed to accept user input (e.g., via physical buttons, touchscreen, etc.), thereby allowing treatment parameters to be set by a health care provider.

In some embodiments, the energy source is controlled without the use of a sensor (e.g., based on the experience of the surgeon or based on a suitable energy output algorithm). In other embodiments, a sensor is used in conjunction with the energy source to provide feedback regarding the amount of energy being directed to the bonding site, and this feedback can be used to adjust the energy source output. For example, in certain embodiments, the sensor is a temperature sensor which detects the amount of heat at the bonding site. In these embodiments, suitable software can be employed to adjust the output of the energy source based on input from the temperature sensor. The sensor may be provided, for example, in the same device as the energy source or in a device that is different from the device containing the energy source. The sensor may be provided, for example, in a medical device that is used for mesh delivery (either with or without the energy source).

A variety of bonding materials can be used in conjunction with the present disclosure.

In this regard, laser tissue soldering processes are known in the surgical art whereby tissue is bonded by applying a solder (commonly, a biological polymer) to the tissue after which a laser is used to activate the solder and form a bond. Without wishing to be bound by theory, it has been reported that the mechanism of laser tissue soldering appears to include a heating-induced protein denaturation-renaturation process. See, e.g., B. Forer et al., *Laryngoscope* 116: June 2006, 1002-1006.

In some embodiments solder materials are used in the present disclosure as bonding materials to bond mesh materials to tissue surfaces, for example, by the application of heat to a solder material while it is in contact with mesh material and a tissue surface, such that the mesh material is fastened onto one or more desired locations on the tissue surface. As indicated above, beneficial energy sources for the application of heat include light sources (e.g., lasers, etc.), radiofrequency sources (e.g., microwave sources, etc.) and plasma sources (e.g., argon beams, etc.), among others.

Particularly beneficial solder materials have a relatively low activation temperature, and are bio-absorbable. Over time (typically between about 4 and 30 days, depending on the solder that is used), the solder may be bioabsorbed, leaving only mesh and tissue growth behind.

Specific solder materials for use in conjunction with the present disclosure include solders of biological origin and synthetic solders. Examples of solders of biological origin include those based on biological polymers, for example, polypeptides including nano-peptides and proteins such as albumin, collagen, elastin and fibrin, protein derivatives, as well as polysaccharides including chitosan, among others. Examples of solders of synthetic origin include polylactide, polyglycolide, poly(glycerol sebacate acrylate), and poly(lactide-co-glycolide). In some embodiments, two, three, four or more solder materials such as those described above are employed. Specific examples include a combination of albumin and collagen, a combination of albumin and chitosan, a combination of collagen and chitosan, and a combination of albumin, collagen, and chitosan, among many other possible combinations.

In some embodiments, at least one energy absorber is used within the solder material to enhance heating efficiency and/or heat distribution within the solder material. Energy absorbers include chromophores, for example, light-specific dyes such as indocyanine green (ICG), fluorescein, basic fuchsin, and fen, nano-gold (e.g., gold nanorods, gold nanoshells, gold nanocages, etc.), SPIONs (superparamagnetic iron oxide nanoparticles), and silica nanoparticles, among other materials. Specific examples include ICG-doped albumin, fluorescein-dye-doped albumin, and nano-gold-doped albumin, among many others.

Photochemical tissue bonding processes are known in the surgical art. These processes take advantage of the photochemical reactions that occur at intimately associated tissue surfaces, which are stained with a photo sensitizing dye (e.g., dyed tissue surfaces which are placed in contact with one another). Without wishing to be bound by theory, it is believed that the dye absorbs photons of visible radiation and promotes the formation of covalent bonds between molecules on the approximated tissue surfaces. For example, reactive species that are produced upon light activation of the dye can react with potential electron donors and acceptors such as amino acids in proteins (e.g., tryptophan, tyrosine, cysteine, and so forth). In this regard, photochemical methods have been reported to form crosslinks in collagen type I molecules. See, Barbara P. Chan et al., *Journal of Surgical Research* 108, 77-84 (2002).

In certain aspects of the present disclosure, photosensitizing dyes are used to bond mesh materials to tissue surfaces, for example, by the application of light of a suitable wavelength to a photosensitizing dye and a solder material (e.g., a biological solder material, including those set forth above, among others) in intimate association with a mesh material and a tissue surface (e.g., a photosensitizing dye admixed with a solder material or coated on a surface of a solder material that is in contact with and disposed between mesh material and tissue), such that the mesh material is fastened onto one or more desired locations on the tissue surface.

A light-emitting energy source such as a low-power laser or light-emitting diode (LED) may be used for this purpose, among others. Specific examples of photosensitizing dyes include one or more of the following: xanthene dyes such as rose bengal, methylene blue and fluorescein, riboflavin dye (e.g., riboflavin-5-phosphate), lumichrome dye, lumiflavin dye, Reactive Black 5, thiazine dye, erythrosine, N-hydroxypyridine-2-(1H)-thione (N-HTP), protoporphyrin I through protoporphyrin IX, coproporphyrins, uroporphyrins, mesoporphyrins, hematoporphyrins and sapphyrins, chlorophylis, e.g., bacteriochlorophyll A, Photofrin®, synthetic diporphyrins and dichlorins, phthalocyanines with or without metal substituents, chloroaluminum phthalocyanine with or without varying substituents, O-substituted tetraphenyl porphyrins, 3,1-meso tetrakis (o-propionamido phenyl) porphyrin, verdins, purpurins, tin and zinc derivatives of octaethylpurpurin, etiopurpurin, hydroporphyrins, bacteriochlorins of the tetra(hydroxyphenyl) porphyrin series (e.g., protoporphyrin I through protoporphyrin IX, coproporphyrins, uroporphyrins, mesoporphyrins, hematoporphyrins and sapphyrins), chlorins, chlorin e6, mono-1-aspartyl derivative of chlorin e6, di-1-aspartyl derivative of chlorin e6, tin(IV) chlorin e6, meta-tetrahydroxphenylchlorin, benzoporphyrin derivatives, benzoporphyrin monoacid derivatives, tetracyanoethylene adducts of benzoporphyrin, dimethyl acetylenedicarboxylate adducts of benzoporphyrin, Diels-Adler adducts, monoacid ring "a" derivative of benzoporphyrin, sulfonated aluminum PC, sulfonated AlPc, disulfonated, tetrasulfonated derivative, sulfonated aluminum naphthalocyanines, naphthalocyanines with or without metal substituents and with or without varying substituents, chlorophylis, bacteriochlorophyll A, anthracenediones, anthrapyrazoles, aminoanthraquinone, phenoxazine dyes, phenothiazine derivatives, chalcogenapyrylium dyes, cationic selena and tellurapyrylium derivatives, ring-substituted cationic PC, pheophorbide derivative, naturally occurring porphyrins, hematoporphyrin, ALA-induced protoporphyrin IX, endogenous metabolic precursors, 5-aminolevulinic acid, benzonaphthoporphyrazines, cationic imminium salts, tetracyclines, lutetium texaphyrin, texaphyrin, tin-etio-purpurin, porphycenes, benzophenothiazinium, eosin, erythrosin, cyanines, merocyanine 540, selenium substituted cyanines, flavins, riboflavin, proflavin, quinones, anthraquinones, benzoquinones, naphthaldiimides, naphthalimides, victoria blue, toluidine blue, dianthroquinones (e.g., hypericin), fullerenes, rhodamines and photosensitive derivatives thereof.

An advantage of using light rather than heat is that there is less risk of causing damage to the tissue (cell death) from heat. Another advantage of using light, rather than heat, to achieve mesh-to-tissue bonding is that complications due to uneven heat distribution can be reduced or eliminated.

In addition, the use of wavelength-specific absorbers such as chromophores enables differential absorption between the chromophore-containing regions and surrounding tissue. One advantage is a selective absorption of radiation by the target, without the need for a precise focusing. Moreover, lower power levels may be used because of the increased absorption of chromophore-containing regions, leading to reduced tissue damage.

Mesh materials for use in accordance with the present disclosure include various synthetic and natural polymers. Beneficial polymers for forming mesh fiber(s) may be selected from the following, among others: (a) polyolefin homopolymers and copolymers, including homopolymers and copolymers of C2-C8 alkenes, for example, polyethylene and polypropylene among others, (b) fluoropolymers, including homopolymers and copolymers of C2-C8 alkenes in which one or more hydrogen atoms are substituted with fluorine, for example, polytetrafluoroethylene (PTFE), polyvinylidene fluoride (PVDF), poly(vinylidene fluoride-co-hexafluoropropene) (PVDF-HFP) among others, (c) polyamides such as nylons, among others, (d) polyesters, including, for example, polyethylene terephthalate, among others, (e) polyurethanes such as polyisobutylene based polyurethanes (PIB-PU) that comprise one or more polyisobutylene segments, among others, (f) polyoxyalkylenes including homopolymers of trioxane (e.g., polytrioxane, also known as polyoxymethylene or acetal) and copolymers of trioxane (e.g., copolymers of trioxane and dioxane) and (g) styrenic copolymers such as alkene-styrene copolymers, including block copolymers comprising one or more polystyrene blocks and one or more polyalkene blocks, for instance, poly(styrene-b-isobutylene-b-styrene) (SIBS), poly(styrene-b-ethylene/butylene-b-styrene) (SEBS).

Mesh materials are commonly in the form of fibers. Consequently, surgical meshes in accordance with the present disclosure may be formed using a variety of fiber-based construction techniques and include, for example, woven meshes and non-woven meshes (e.g., knitted, braided, coiled, randomly wrapped, spunbound, etc.).

The overall fiber width (e.g., the diameter of circular fibers) in the meshes of the present disclosure may vary widely. In certain embodiments, the surgical meshes of the present disclosure may have fiber widths ranging from 50 μm to 200 μm, for example, from 50 μm to 70 μm to 90 μm to 110 μm to 130 μm to 150 μm to 170 μm to 190 μm to 200 μm.

In certain embodiments, fibers may be provided with surface features, for example, to increase the surface area of the fibers and thus the contact area between the fibers and a solder material coating.

Surgical meshes in accordance with the present disclosure may also have a wide range of pore sizes. In various embodiments, the surgical meshes of the present disclosure may have area pore sizes ≥0.25 mm². In various embodiments, the pore size can be varied, for example, to modify tissue in-growth properties. Meshes include Type I meshes, which are macroporous prostheses (i.e., with pores >75 μm), Type II meshes, which are microporous prostheses (i.e., pores <10μ) and Type III meshes, which are macroporous prostheses with multifilamentous or microporous components.

In certain embodiments, meshes may be formed with differing pore sizes in differing areas of the mesh. This may lead to differing tissue ingrowth characteristics in some parts of the mesh relative to others, and may lead to different mesh-tissue interactions (e.g. based on the flexibility of the mesh and tissue). This may also result in differing bonding material densities in some parts of the mesh relative to others. For example, areas of smaller pore size are associated with a higher fiber density and thus higher fiber surface area, which can allow for increased bonding material to be coated onto the fibers in those areas, relative to areas of larger pore size. Higher bonding material density may, in turn, be associated with enhanced bonding in those areas, relative to areas of larger pore size.

In certain embodiments, meshes may be provided with one or more loops along the edges of the mesh (e.g., at the end(s) of one or more arms) to facilitate unraveling and placement of the mesh once inside the body. The loops may be made, for example, of a suitable degradable material.

Bonding material may be associated with mesh material in various ways. For example, mesh material may be admixed or impregnated with bonding material, mesh material may be coated with bonding material, a sheet of bonding material may be laminated to mesh material, and so forth.

The bonding material may be present throughout the entire mesh or on only a portion of the mesh, for instance, associated with 1% or less to 99% or more of the total length of fiber within the mesh (e.g., from 1% to 5% to 10% to 25% to 50% to 75% to 90% to 95% to 99%). The bonding material may be present, for example, on only one side of the mesh but not the other, or may be present only in certain lateral portions of the mesh but not others, for example, being present only at the ends of the mesh, present only at strategic zones along the edges of the mesh, and so forth. In certain embodiments, this allows the mesh to be largely free of bonding material, which reduces bonding material consumption and potentially facilitates tissue growth around the mesh in areas free of bonding material, while nonetheless ensuring that the mesh can be securely attached in those areas where bonding material is present.

In certain embodiments, differing bonding materials may be employed in different areas of the mesh. As one example, different areas of the mesh may be coated with soldering materials having different compositions (e.g. soldering materials having different bioabsorption rates, etc.).

Mesh material may be impregnated and/or coated with bonding material either before a mesh is formed (e.g., when the mesh material is in fiber form) or after a mesh is formed. Mesh material may be impregnated and/or coated with bonding material, for example, using various techniques which may be selected, for example, from dipping techniques, spraying techniques, spin coating techniques, web coating techniques, electrostatic techniques, techniques in which bonding material is selectively applied to certain regions of the mesh but not others, for example, through the use of a suitable application device such as a sprayer, brush, roller, pen, or printer (e.g., screen printing device, ink jet printer, etc.). A partial or complete bonding material coating may also be formed by coextruding the mesh material with bonding material.

Meshes may be provided with an intermediate layer of material between a layer of bonding material and the mesh material, for instance, an intermediate layer may be formed of a suitable polymer, such as an isobutylene-styrene copolymers (e.g., SIBS), among many others.

In certain embodiments, meshes in accordance with the present disclosure may be at least partially covered with a removable thin film. This film prevents the mesh from sticking to itself or to other objects during delivery. The film may be peeled off the mesh once in use, for example, inside the body. The film may comprise, for example, a material such as a fluoropolymer (see, e.g., the fluoropolymers listed above). The film may be provided with features that allow the film to be more easily gripped (e.g., loops, etc.), thereby facilitating removal of the film from the mesh. In other embodiments, the film may be formed from a soluble material that can be removed upon application of a suitable fluid, for example, saline, among other possibilities. In still other embodiments, the film may be formed from a material that degrades upon application of energy that is employed to activate the bonding material.

Surgical meshes in accordance with the present disclosure include a variety of meshes for soft tissue repair, including meshes for pelvic floor repair, vaginal slings, meshes for renal pelvis repair, urethral slings, meshes for fecal incontinence, hernia meshes (e.g., meshes for inguinal hernia, hiatus hernia, etc.), meshes for thoracic wall defects, breast support meshes and various other soft-tissue surgical support meshes, including meshes for cosmetic and reconstructive surgery, among others. Depending on the procedure, meshes in accordance with the present disclosure may be implanted by one or more of the following routes, among others: transluminally, for instance, transvaginally (e.g., by vaginal incision), laparoscopically, via open abdominal surgery (laparotomy), transrectally, transcystoscopically, and percutaneously. Surgical meshes may be surgically implanted in a variety of subjects, typically vertebrate subjects, more typically mammalian subjects, including human subjects, pets and livestock.

Figure 1:
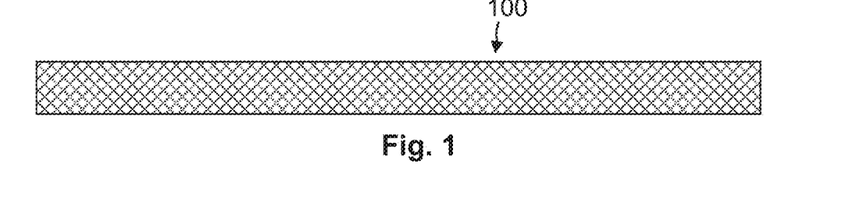
FIG. 1 is a schematic illustration of a surgical mesh, in accordance with an embodiment of the present invention.

Turning now to the drawings, there is schematically illustrated in FIG. 1, a mesh 100, which may be useful as a urethral sling for the treatment of SUI. The mesh 100 may comprise a fiber mesh material which is associated with a bonding material (e.g., a solder material, which may or may not be associated with a photosensitizing dye, etc.), for instance, a coating of bonding material that covers all or a portion of the mesh, among other possibilities.

Figure 2:
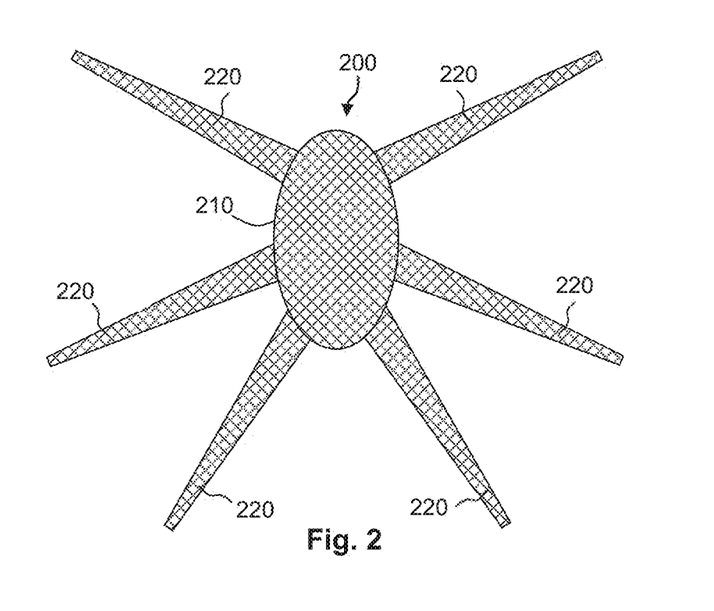
FIG. 2 is a schematic illustration of a surgical mesh, in accordance with another embodiment of the present invention.

In accordance with another embodiment, there is schematically illustrated in FIG. 2 a mesh 200, for example, a pelvic floor repair mesh, having a central body portion 210 and a plurality of arms 220 that emanate from the central portion 210. As above, the mesh 200 may comprise a fiber mesh material which is associated with a bonding material, for example, a coating of bonding material that covers all or a portion of the mesh, among other options. Although the mesh of FIG. 2 has two rectangular arms and an oval central body portion, other body and arm shapes may be used, and other numbers of arms may be used (e.g., 3, 4, 5, 6, 7, 8, etc.).

Figure 3:
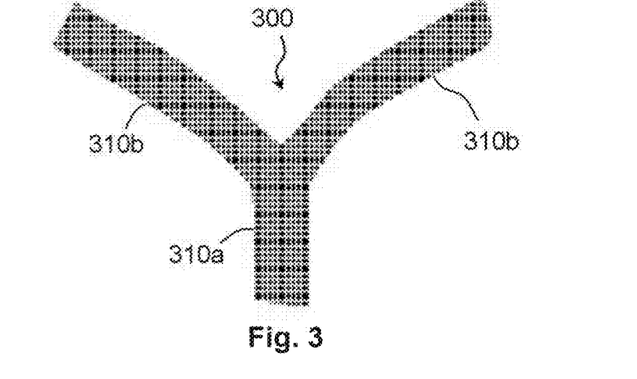
FIG. 3 is a schematic illustration of a surgical mesh, in accordance with yet another embodiment of the present invention.

In accordance with another embodiment, there is schematically illustrated in FIG. 3 a surgical mesh 300, specifically a Y-shaped mesh, having arms 310a and 310b. As elsewhere herein, the mesh 300 may comprise a fiber mesh material with an associated bonding material.

Figures 4A, 4B:
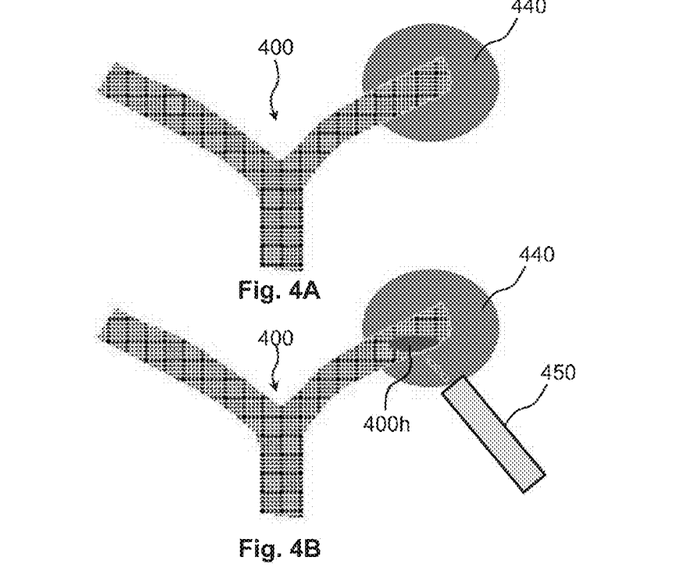
FIGS. 4A-4B are schematic illustrations showing a medical procedure for implanting surgical mesh, in accordance with an embodiment of the present invention.

Various methods may be used in accordance with the present disclosure to attach meshes to tissue. As previously noted, these methods avoid the need for mechanical fasteners such as sutures, staples, and so forth. FIGS. 4A-4B are schematic illustrations of a medical procedure for attaching a surgical mesh, in accordance with an embodiment of the present disclosure. As shown in FIG. 4A, a mesh 400 with an associated bonding material, such as a solder material and/or a photosensitizing dye, is placed in contact with tissue 440. Then, as shown in FIG. 4B, an energy source 450 is used to supply energy (e.g., heat and/or light) to the mesh 400 and tissue 440 in area 400h, causing the mesh 400 to become attached to the tissue 440 in area 400h. The entire mesh or only a portion thereof may be associated with bonding material as described elsewhere herein.

In the preceding embodiment, the mesh and the bonding material are applied to the tissue simultaneously (e.g., the mesh material is coated, impregnated or otherwise associated with the bonding material).

In some embodiments, bonding material is applied to the site independently of the mesh, in which case the mesh either may be associated with bonding material at the time of application or free of bonding material at the time of application. In these embodiments, the bonding material may be applied to tissue followed by the mesh, or the mesh may be applied to tissue followed by the bonding material. The independently applied bonding material may be applied in solid form, liquid form or a combination thereof. For instance, the independently applied bonding material may be applied in the form of a fluid such as a liquid, paste or gel (e.g., an organic or aqueous liquid, paste or gel comprising a solder material and/or photosensitizing dye) or may be applied as a solid (e.g., a porous or non-porous film that includes a solder material and/or photosensitizing dye, for instance, a solid film with raised sections (e.g., similar to a block) that can be fitted/plugged into the mesh). For example, with reference to FIG. 4B, the independently applied bonding material may be applied only in the area 400*h*.

Regardless of whether the mesh and the bonding material are applied to the tissue simultaneously or independently, in some embodiments, a mask may be temporarily disposed between the energy source and the mesh (e.g., overlaid on the mesh), thereby shielding some locations of the mesh from energy while permitting other locations to be exposed to energy, thereby activating the solder in those locations.

As noted above, meshes are attached to tissue during the course of a variety of surgical procedures, including various urogynecological procedures. Sacrocolpopexy is one such procedure, which may be used to repair pelvic organ prolapse. This procedure can be performed, for example, using an open abdominal technique or through the use of minimally invasive surgery, such as laparoscopy, trans-vaginal surgery, or combinations of the same. The procedure may make use of a mesh that includes three arms, for instance, a Y-shaped mesh such as that shown in FIG. 3. In the procedure, one arm of the mesh (e.g., one of arms 310*b*) is attached to the anterior vaginal wall, another arm (e.g., the other of arms 310*b*) is attached to the posterior vaginal wall, and a third arm (e.g., arm 310*a*) is attached to tissues adjacent the sacrum, for example, the sacral promontory.

In the present disclosure, the arms are attached using tissue bonding, which may save significant amounts of time and improve implanted mesh properties relative to current methods in which the mesh is attached to tissue using sutures. For example, in a typical procedure, approximately 6 suture knots are used to attach a mesh portion to each side of the vaginal wall, and another 2-4 knots are used to attach the mesh adjacent to the sacrum. The creation of suture knots is time-consuming, typically consuming between 3-8 minutes per knot. Moreover, in procedures where sutures are used to attach meshes, a mesh may bunch, which can constrain the mesh properties.

Figure 5:
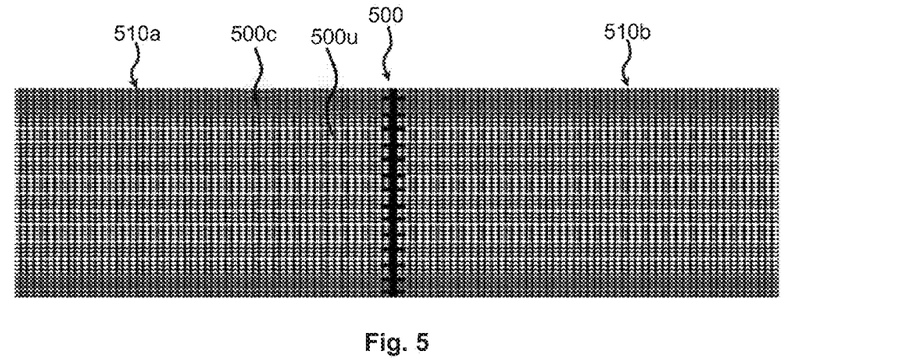
FIGS. 5-8 are schematic illustrations of meshes, in accordance with various additional embodiments of the present invention.

As previously noted, bonding material may be associated with an entire mesh or with only a portion of a mesh. For instance, in some embodiments, bonding material may be applied to only one side of a mesh. In other embodiments, bonding material may be associated with certain portions along the length of the mesh, but not others. For example, in accordance with an embodiment illustrated in FIG. 5, a mesh 500 is shown having arms 510*a*, 510*b*. In FIG. 5, certain portions 500*c* of the mesh 500 are provided with bonding material (i.e., portions along the lateral edges of the arms) whereas the remaining portions 500*u* of the mesh 500 are not provided with bonding material. In one particular embodiment, the mesh is a Y-shaped mesh wherein the arm 510*a* is configured, for example, for attachment to tissues adjacent the sacrum, for example, the sacral promontory, in a sacrocolpopexy procedure while arms 510*b* (one arm shown) are configured, for example, for attachment to the vaginal anterior and/or posterior wall.

Figure 6:
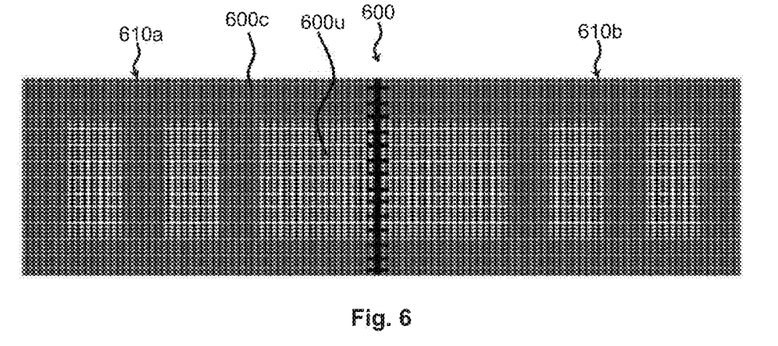

In accordance with another embodiment illustrated in FIG. 6, a mesh 600 is shown having arms 610*a*, 610*b*. In FIG. 6, certain portions 600*c* of the mesh 600 are provided with bonding material (i.e., portions along the lateral edges of the arms, portions along the end edges of the arms, and portions traversing the arms) whereas remaining portions 600*u* of the mesh 600 (e.g., certain interior areas of the mesh) are not provided with bonding material. As with the mesh of FIG. 5, in one particular embodiment, the mesh is a Y-shaped mesh wherein the arm 610*a* is configured, for example, for attachment to tissues adjacent the sacrum, for example, the sacral promontory, in a sacrocolpopexy procedure while arms 610*b* (one arm shown in FIG. 6) are configured, for example, for attachment to the vaginal anterior and/or posterior wall.

Figure 7:
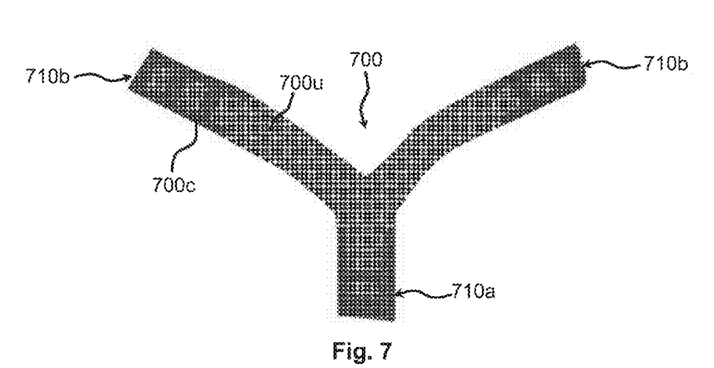

Another mesh of this type is illustrated in FIG. 7, in which a Y-shaped mesh 700 is shown having arms 710*a*, 710*b* in which some portions 700*c* of the mesh 700 are provided with bonding material (i.e., portions along the lateral edges near the ends of the arms, portions along the end edges of the arms, and portions traversing the arms) while other portions 700*u* of the mesh 700 are not provided with bonding material. As above, in a particular embodiment, arm 710*a* may be configured, for example, for attachment to tissues adjacent the sacrum, for example, the sacral promontory, in a sacrocolpopexy procedure while arms 710*b* may be configured, for example, for attachment to the vaginal anterior and/or posterior wall.

Figure 8:
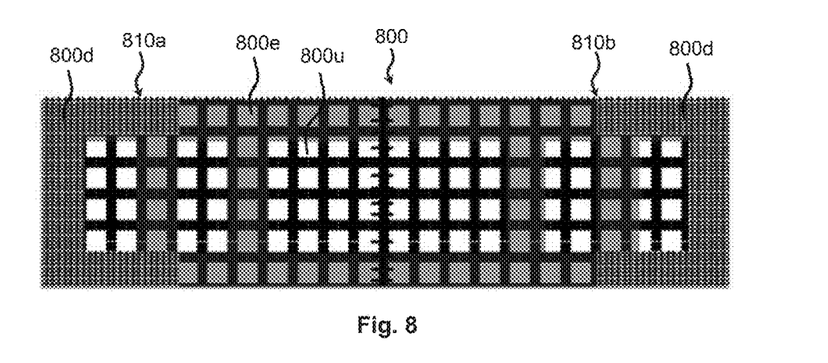

In accordance with yet another embodiment illustrated in FIG. 8, a mesh 800 is shown having arms 810*a*, 810*b*. In FIG. 8, some portions 800*e* of the mesh 800 are of larger pore size and are provided with bonding material (i.e., portions along lateral edges of the arms and portions traversing the arms), other portions 800*d* of the mesh 800 are of smaller pore size and are provided with bonding material (i.e., portions along lateral edges of the arms and portions along end edges of the arms), and still other portions 800*u* of the mesh 800 (e.g., portions in the interior of the mesh) are not provided with bonding material. As with the meshes in FIGS. 5-7, in a particular embodiment, the mesh 800 may be configured for use in a sacrocolpopexy procedure.

In certain embodiments, the meshes of the present disclosure may comprise various additional agents other than those discussed above, including therapeutic agents and imaging agents, among other possible agents. Such agents may be, for example, incorporated into all or a portion of the mesh material, or such agents may be applied in a coating (e.g., admixed with a bonding material or applied independently of a bonding material) over all or a portion of the mesh material, among other strategies.

"Therapeutic agents," drugs," "bioactive agents" "pharmaceuticals," "pharmaceutically active agents" and other related terms may be used interchangeably herein. Therapeutic agents may be used singly or in combination.

In certain embodiments, the meshes of the present disclosure may comprise one or more therapeutic agents, for example, selected from the following, among many others: (a) female hormones such as estrogen (including estrogen cocktails) and progesterone, (b) anti-inflammatory agents including corticosteroids such as hydrocortisone and prednisolone, and non-steroidal anti-inflammatory drugs (NSAIDS) such as aspirin, ibuprofen, and naproxen; (c) narcotic and non-narcotic analgesics and local anesthetic agents (e.g., for purposes of minimizing pain); (d) growth factors such as epidermal growth factor and transforming growth factor-α (e.g., for purposes of stimulate the healing process and or promoting growth of collagenous tissue); (e)

antimicrobial agents including chlorhexidine, triclosan, nitrofurazone, benzalkonium chlorides, silver salts, silver particles, metallic silver and antibiotic agents such as the penicillins (e.g., penicillin G, methicillin, oxacillin, ampicillin, amoxicillin, ticarcillin, etc.), the cephalosporins (e.g., cephalothin, cefazolin, cefoxitin, cefotaxime, cefaclor, cefoperazone, cefixime, ceftriaxone, cefuroxime, etc.), the carbapenems (e.g., imipenem, metropenem, etc.), the monobactems (e.g., aztreonem, etc.), the carbacephems (e.g., loracarbef, etc.), the glycopeptides (e.g., vancomycin, teichoplanin, etc.), bacitracin, polymyxins, colistins, fluoroquinolones (e.g., norfloxacin, lomefloxacin, fleroxacin, ciprofloxacin, enoxacin, trovafloxacin, gatifloxacin, etc.), sulfonamides (e.g., sulfamethoxazole, sulfanilamide, etc.), diaminopyrimidines (e.g., trimethoprim, etc.), rifampin, aminoglycosides (e.g., streptomycin, neomycin, netilmicin, tobramycin, gentamicin, amikacin, etc.), tetracyclines (e.g., tetracycline, doxycycline, demeclocycline, minocycline, etc.), spectinomycin, macrolides (e.g., erythromycin, azithromycin, clarithromycin, dirithromycin, troleandomycin, etc.), and oxazolidinones (e.g., linezolid, etc.), (f) anti-collagenase agents (collagenase inhibitors) including tetracycline compounds such as doxycycline, bacitracin, prednisolone, medroxyprogesterone, cysteine, acetylcysteine, N-acetylcysteine, sodium citrate, edetic acid (EDTA), TIMP-1 and TIMP-2, (g) anti-elastase agents (elastase inhibitors) such as alpha-1-protease inhibitor, alpha-1-antitrypsin, secretory leukocyte protease inhibitor, glycosaminoglycans (e.g., heparin), elastase inhibitor I, elastase inhibitor II, elastase inhibitor III, elastase inhibitor IV, peptide aldehydes, caffeic acid, elafin, ceramides, nicardipine, procyanidins, proanthocyanidins, coumarinic derivatives, sivelestat (e.g., sivelestat sodium salt), 6-amino-2-phenyl-4H-3,1-benzoxazin-4-one aminoacyl, and dipeptidyl derivatives, (h) pharmaceutically acceptable salts, esters and other derivatives of the foregoing, and (i) combinations of two or more of the foregoing.

Additional agents for use in conjunction with the meshes of the present disclosure also include imaging agents including (a) contrast agents for use in connection with x-ray fluoroscopy, including metals, metal salts and oxides (particularly bismuth salts and oxides), and iodinated compounds, among others, (b) contrast agents for use in conjunction with ultrasound imaging, including organic and inorganic echogenic particles (i.e., particles that result in an increase in the reflected ultrasonic energy) or organic and inorganic echolucent particles (i.e., particles that result in a decrease in the reflected ultrasonic energy), and (c) contrast agents for use in conjunction with magnetic resonance imaging (MRI), including contrast agents that contain elements with relatively large magnetic moment such as Gd(III), Mn(II), Fe(III) and compounds (including chelates) containing the same, such as gadolinium ion chelated with diethylenetriaminepentaacetic acid.

In various embodiments, the mesh may contain from less than 1 wt % to 50 wt % or more of one or more of the preceding additional agents.

In another aspect of the disclosure, medical kits useful in treating a patient in need of tissue repair are provided. The medical kits may include all or a subset of all the components useful for treating a patient. For example, the medical kits may comprise any combination of any two, three, four, or more of the following items: (a) a surgical mesh in accordance with the present disclosure, either without or with an associated bonding material, (b) a bonding material in accordance with the present disclosure, in liquid, paste or gel form (e.g., containing a solder material and/or a photosensitizing dye material dissolved and/or suspended in a solution, paste or gel) or in solid form (e.g., in the form of a continuous sheet, porous sheet, etc., that contains a solder material and/or a photosensitizing dye material), (c) a surgical instrument (e.g., one that can hold and place a surgical mesh), (d) an energy source (e.g., in a stand-along unit or associated with an energy sensor and/or associated with a surgical instrument), (e) suitable packaging material, and (f) printed material with one or more of the following: (i) storage information and (ii) instructions regarding how to implant the surgical mesh in a subject.

Although various embodiments are specifically illustrated and described herein, it will be appreciated that modifications and variations of the present disclosure are covered by the above teachings and are within the purview of the appended claims without departing from the spirit and intended scope of the invention.

What is claimed is:

1. A surgical mesh comprising:
   a mesh material including a first arm configured to be attached to an anterior vaginal wall, a second arm configured to be attached to a posterior vaginal wall, and a third arm configured to be attached to tissue adjacent to a sacrum; and
   a light-activated bonding material associated with the first arm, the second arm, and the third arm, the light-activated bonding material including a tissue solder material and a wavelength-specific energy absorber, the wavelength-specific energy absorber including chromophores, the light-activated bonding material including first light-activated bonding material disposed on an edge portion of the first arm, and second light-activated bonding material disposed on a portion traversing the first arm, the second light-activated bonding material being disposed a distance away from the first light-activated bonding material, wherein a portion of the first arm that extends between the edge portion and the portion traversing the first arm is devoid of light-activated bonding material,
   wherein the light-activated bonding material is configured to bond to tissue when exposed to light having a wavelength that corresponds to the wavelength-specific energy absorber.

2. The surgical mesh of claim 1, wherein the light-activated bonding material also includes a photosensitizing dye, the photosensitizing dye admixed with the tissue solder material.

3. The surgical mesh of claim 1, wherein the tissue solder material is selected from chitosan, albumin, collagen, elastin, fibrinogen, nano-peptides, derivatives of the foregoing, and combinations of two or more of the foregoing, wherein the bonding material also includes a photosensitizing dye selected from rose bengal dye, methylene blue dye, fluorescein dye, xanthene dye, riboflavin dye, lumichrome dye, lumiflavin dye, Reactive Black 5 dye, and combinations of two or more of the foregoing.

4. The surgical mesh of claim 1, wherein the mesh material includes fibers with surface features to increase a surface area of the fibers and a contact area between the fibers and the tissue solder material.

5. The surgical mesh of claim 1, wherein the tissue solder material is bioabsorbable.

6. The surgical mesh of claim 1, wherein a portion of the first arm includes a coating of the light-activated bonding material over the mesh material.

7. The surgical mesh of claim 1, wherein the first arm includes a first lateral edge portion, and a second lateral edge portion, the first lateral edge portion being disposed perpendicular to the edge portion, the second lateral edge portion being disposed parallel to the first lateral edge, the light-activated bonding material including third light-activated bonding material disposed on the first lateral edge portion, and fourth light-activated bonding material disposed on the second lateral edge portion, wherein a portion of the first arm that extends between the first lateral edge portion and the second lateral edge portion is devoid of light-activated bonding material.

8. The surgical mesh of claim 1, wherein the first arm has a first surface and a second surface opposite to the first surface, the second surface being separated by a thickness of the first arm, wherein the light-activated bonding material is applied on the first surface but not the second surface.

9. The surgical mesh of claim 1, wherein the first arm includes a first area having a first pore size, a second area having a second pore size, and a third area, the first pore size being different than the second pore size, wherein the light-activated bonding material is applied to the first area and the second area but not the third area.

10. The surgical mesh of claim 1, further comprising:
one or more loops attached to the mesh material; and
a film configured to be removed from the mesh material in use.

11. A method of attaching a urogynecological surgical mesh to patient tissue comprising:
placing a first arm of a mesh material in contact with an anterior vaginal wall, the first arm having a first portion that includes a light-activated bonding material, the light-activated bonding material having a tissue solder material and a wavelength-specific energy absorber, the wavelength-specific energy absorber including chromophores;
covering a second portion of the first arm with a mask, the second portion of the first arm being devoid of light-activated bonding material;
attaching the first arm to the anterior vaginal wall by applying light from a light energy source to the light-activated bonding material on the first portion of the first arm while the mask shields the second portion of the first arm from the light from the light energy source;
placing a second arm of the mesh material in contact with a posterior vaginal wall, the second arm including the light-activated bonding material;
attaching the second arm to the posterior vaginal wall by applying light from the light energy source to the light-activated bonding material of the second arm;
placing a third arm of the mesh material in contact with tissue adjacent to a sacrum, the third arm including the light-activated bonding material; and
attaching the third arm to the tissue adjacent to the sacrum by applying light from the light energy source to the light-activated bonding material of the third arm.

12. The method of claim 11, wherein the light energy source includes a light-emitting diode (LED).

13. The method of claim 11, wherein the light-activated bonding material of the first arm is provided in a coating over the first portion the first arm.

14. The method of claim 11, wherein the light-activated bonding material of the first arm and the first arm are separately placed into contact with the anterior vaginal wall.

15. The method of claim 11, wherein the light-activated bonding material of the first arm is in the form of a liquid composition, gel composition, a separate film, or a combination thereof.

16. The method of claim 11, wherein the first arm of the mesh material is applied to the anterior vaginal wall using a surgical instrument.

17. The method of claim 11, wherein an amount of light applied by the light energy source is monitored with a temperature sensor and is adjusted based on feedback from the temperature sensor.

18. A kit comprising:
a surgical mesh having a first arm configured to be attached to an anterior vaginal wall, a second arm configured to be attached to a posterior vaginal wall, and a third arm configured to be attached to tissue adjacent to a sacrum;
a light-activated bonding material associated with the first arm, the second arm, and the third arm, the light-activated bonding material having a tissue solder material, the light-activated bonding material including a wavelength-specific energy absorber, the wavelength-specific energy absorber including chromophores, the light-activated bonding material including first light-activated bonding material disposed on an edge portion of the first arm, and second light-activated bonding material disposed on a portion traversing the first arm, the second light-activated bonding material being disposed a distance away from the first light-activated bonding material, wherein a portion of the first arm that extends between the edge portion and the portion traversing the first arm is devoid of light-activated bonding material, wherein different areas of the surgical mesh are coated with solder materials having different bioabsorption rates;
a surgical instrument configured to hold and place the surgical mesh;
a light energy source configured to apply light having a wavelength corresponding to the wavelength-specific energy absorber to the light-activated bonding material.

* * * * *